United States Patent
Lin et al.

(10) Patent No.: US 12,018,018 B2
(45) Date of Patent: Jun. 25, 2024

(54) PREGABALIN LACTAM METHYLENE DIMER AND PREPARATION METHOD THEREFOR

(71) Applicants: Zhejiang Huahai Pharmaceutical Co., Ltd, Zhejiang (CN); Zhejiang Huahai Zhicheng Pharmaceutical Co., Ltd., Zhejiang (CN)

(72) Inventors: Jinsheng Lin, Zhejiang (CN); Xiaofei Liu, Zhejiang (CN); Dan Li, Zhejiang (CN); Jing Wang, Zhejiang (CN); Yue Li, Zhejiang (CN); Wenquan Zhu, Zhejiang (CN); Wenbin Chen, Zhejiang (CN); Min Li, Zhejiang (CN)

(73) Assignees: Zhejiang Huahai Pharmaceutical Co., Ltd, Zhejiang (CN); Zhejiang Huahai Zhicheng Pharmaceutical Co., Ltd., Zhejiang (CN)

( * ) Notice: Subject to any disclaimer, the term of this patent is extended or adjusted under 35 U.S.C. 154(b) by 643 days.

(21) Appl. No.: 17/291,237

(22) PCT Filed: Nov. 6, 2018

(86) PCT No.: PCT/CN2018/114113
§ 371 (c)(1),
(2) Date: May 4, 2021

(87) PCT Pub. No.: WO2020/093229
PCT Pub. Date: May 14, 2020

(65) Prior Publication Data
US 2021/0387971 A1    Dec. 16, 2021

(51) Int. Cl.
*C07D 403/06* (2006.01)

(52) U.S. Cl.
CPC ................ *C07D 403/06* (2013.01)

(58) Field of Classification Search
CPC .................................. C07D 403/06
See application file for complete search history.

(56) References Cited

U.S. PATENT DOCUMENTS

| | | |
|---|---|---|
| 2017/0192298 A1 | 7/2017 | Xie |
| 2017/0285401 A1 | 10/2017 | Cui et al. |
| 2018/0031914 A1 | 2/2018 | Xie |

FOREIGN PATENT DOCUMENTS

| | | |
|---|---|---|
| CN | 101561610 A | 10/2009 |
| CN | 104829515 A | 8/2015 |
| IN | 3016/MU/2013 | 7/2015 |
| JP | 2009/086113 A | 4/2009 |
| KR | 10-2006-0040089 A | 5/2006 |

OTHER PUBLICATIONS

Tian et al., "Structure elucidation and formation mechanistic study of a methylenebridged pregabalin dimeric degradant in pregabalin extended-release tablets", International Journal of Pharmaceutics, vol. 575, 2020, pp. 1-9.

*Primary Examiner* — Shawquia Jackson
(74) *Attorney, Agent, or Firm* — Seed IP Law Group LLP

(57) ABSTRACT

Provided are a pregabalin lactam methylene dimer and a preparation method therefor. The method comprises the following steps: dissolving pregabalin in a reaction solvent, reacting same with an aldehyde in an acidic system and isolating the obtained target product pregabalin lactam methylene dimer. The preparation method for pregabalin lactam methylene dimer provided by the present application has a simple operation, a high product yield, a good purity and a low cost.

15 Claims, 3 Drawing Sheets

PREGABALIN LACTAM METHYLENE DIMER AND PREPARATION METHOD THEREFOR

FIELD OF THE INVENTION

The present application relates to the technical field of pharmaceutical manufacturing, in particular to pregabalin lactam methylene dimer and a preparation method thereof.

BACKGROUND OF THE INVENTION

Pregabalin, the chemical name of which is (S)-3-aminomethyl-5-methylhexanoic acid, the molecular formula of which is C8H17NO2, and the molecular weight of which is 159.23, is of a structural formula as follows:

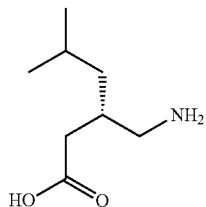

The trade name of pregabalin is Lyrica3, (S)-3-aminomethyl-5-methylhexanoic acid, the molecular formula of which i as the first drug jointly certified by the United States and Europe for the treatment of two types of neuralgia, the main indications of which include diabetic peripheral neuralgia, postherpetic neuralgia, fibromyalgia, and neuropathic pain associated with spinal cord injury.

SUMMARY OF THE INVENTION

In the process of studying the long-term stability and the accelerated stability of pregabalin tablets, the inventors discovered that there is an unknown impurity in the pregabalin tablets. The content of this impurity in the sample of pregabalin tablets for long-term stability and accelerated stability is relatively high. The peak area of this impurity generally accounts for about 0.10-0.70%, and the content of this impurity will continue to increase as the storage time increased. If the prescription parameters are not controlled properly, this impurity can easily exceed the unknown individual impurity limit index of 0.20%.

After high resolution mass spectrometry and nuclear magnetic resonance characterization, this impurity is determined to be pregabalin lactam methylene dimer, structural formula of which is as follows:

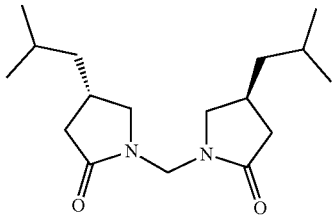

In the development of analysis method of pregabalin tablets and the subsequent finished product inspection process, it is necessary to use a standard substance of this impurity to locate and quantify this impurity in pregabalin tablets. Therefore, a large amount of the standard substance of pregabalin lactam methylene dimer will be used.

In order to prepare the pregabalin lactam methylene dimer, a traditional impurity separation method can be used: separating the target impurity (pregabalin lactam methylene dimer) from a sample that is forcibly degraded or a sample for long-term stability of pregabalin tablets. However, the target impurity can only reach a content of 0.7% as detected by HPLC (High Performance Liquid Chromatography), and there are many similar impurities with similar contents in the sample. At the same time, the presence of adjuvants will also interfere with the separation. The period for a separation is long, and the pure product will be obtained through multiple separations, generally with a total yield of only about 0.3%.

Based on the above, the present application provides a pregabalin lactam methylene dimer and a preparation method thereof. The technical solutions are as follows:

The present application provides a pregabalin lactam methylene dimer, which has following structural formula:

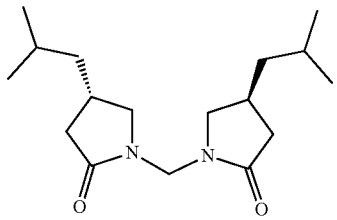

The present application also provides a simple and efficient method for preparing the pregabalin lactam methylene dimer, comprising following steps:
(a) adding pregabalin, an acid and an aldehyde to a reaction solvent to obtain a reaction system;
(b) heating the reaction system to a temperature of 30-100° C. to react for 0.5-36 hours;
(c) obtaining the pregabalin lactam methylene dimer after the reaction is completed.

In some embodiments of the present application, the reaction solvent in step (a) is selected from the group consisting of water, a polar organic solvent, and a mixture of water and the polar organic solvent.

In some embodiments of the present application, the polar organic solvent is selected from the group consisting of methanol, ethanol, propanol, isopropanol, acetonitrile, acetone, N,N-dimethylformamide, dimethylsulfoxide and N-methylpyrrolidone, or any combination thereof.

In some embodiments of the present application, the acid in step (a) is selected from the group consisting of organic acid, inorganic acid, and a combination thereof.

In some embodiments of the present application, the organic acid is selected from the group consisting of formic acid, acetic acid, trifluoroacetic acid, methanesulfonic acid, ethanesulfonic acid, benzenesulfonic acid and p-toluenesulfonic acid, or any combination thereof.

In some embodiments of the present application, the inorganic acid is selected from the group consisting of hydrochloric acid, sulfuric acid, and phosphoric acid, or any combination thereof. In specific embodiments, diluted hydrochloric acid, diluted sulfuric acid, diluted phosphoric acid, and the like can be used.

In some embodiments of the present application, the aldehyde is selected from the group consisting of formaldehyde, formaldehyde dimer, metaformaldehyde and paraformaldehyde, or any combination thereof.

In some embodiments of the present application, the aldehyde is formaldehyde or metaformaldehyde.

In some embodiments of the present application, a molar ratio of the acid to pregabalin in step (a) is 0.01:1-50:1.

In some embodiments of the present application, a molar ratio of the acid to pregabalin in step (a) is 0.1:1-2.5:1.

In some embodiments of the present application, a molar ratio of the acid to pregabalin in step (a) is 0.1:1-1.6:1.

In some embodiments of the present application, a molar ratio of the aldehyde to pregabalin in step (a) is 0.1:1-10:1.

In some embodiments of the present application, a molar ratio of the aldehyde to pregabalin in step (a) is 0.3:1-3:1.

In some embodiments of the present application, a molar ratio of the aldehyde to pregabalin in step (a) is 0.3:1-1.1:1.

In some embodiments of the present application, the temperature of the reaction system in step (b) is 55-75° C., and the reaction is performed for 12-24 hours.

In some embodiments of the present application, step (c) comprises: removing the reaction solvent after the reaction is completed, and separating the solid to obtain pregabalin lactam methylene dimer.

In some embodiments of the present application, separating is performed by column chromatography or preparative liquid chromatography.

In some embodiments of the present application, the reaction system is detected by HPLC at the end of the reaction, in which the content of the pregabalin lactam methylene dimer is about 43-55%.

In some embodiments of the present application, the pregabalin lactam methylene dimer separated in step (c) is detected by HPLC, the purity of which can reach equal to or more than 99.0%.

The pregabalin lactam methylene dimer prepared in the present application is detected by hydrogen nuclear magnetic resonance spectroscopy and carbon nuclear magnetic resonance spectroscopy. The hydrogen nuclear magnetic resonance spectroscopy and carbon nuclear magnetic resonance spectroscopy are shown in FIG. 1, Table 1, FIG. 2, and Table 2, respectively. The numbers of atoms in compound are shown in FIG. 3.

Table 1 is the analysis of the hydrogen nuclear magnetic resonance spectroscopy of the pregabalin lactam methylene dimer prepared in the present application.

TABLE 1

| Proton Type | Chemical Shift (ppm) | Peak Type | Assignment H No. | Proton Number |
|---|---|---|---|---|
| C-H | 0.77 | d | H-7/8/16/17 | 12 |
| C-H | 1.18 | t | H-5/14 | 4 |
| C-H | 1.44 | m | H-6/15 | 2 |
| C-H | 1.93, 2.38 | d | H-2/11 | 4 |
| C-H | 2.28 | m | H-3/12 | 2 |
| C-H | 2.85, 3.38 | dd | H-4/13 | 4 |
| C-H | 4.62 | s | H-9 | 2 |

Table 2 is the analysis of the carbon nuclear magnetic resonance spectroscopy of the pregabalin lactam methylene dimer prepared in the present application.

TABLE 2

| Chemical Shift (ppm) | C Atom Type | C Number | Assignment C No. |
|---|---|---|---|
| 22.5 | $CH_3$ | 4 | C-7/8/16/17 |
| 25.9 | CH | 2 | C-6/15 |
| 29.7 | CH | 2 | C-3/12 |

TABLE 2-continued

| Chemical Shift (ppm) | C Atom Type | C Number | Assignment C No. |
|---|---|---|---|
| 37.5 | $CH_2$ | 2 | C-2/11 |
| 43.8 | $CH_2$ | 2 | C-5/14 |
| 48.9 | $CH_2$ | 1 | C-9 |
| 52.3 | $CH_2$ | 2 | C-4/13 |
| 175.4 | C | 2 | C-1/10 |

The pregabalin lactam methylene dimer prepared in the present invention is detected by combined high performance liquid chromatograph-high resolution mass spectrometry (HPLC-HRMS), the [M+H$^+$] accurate molecular weight of which is 295.2380, the [M+K$^+$] accurate molecular weight of which is 333.1943, and the matched molecular formula of which is $C_{17}H_{30}N_2O_2$, as shown in FIG. 4.

It can be determined through the above-mentioned structural characterization that the method provided by the present application realizes the preparation of the pregabalin lactam methylene dimer.

The pregabalin lactam methylene dimer provided by the present application has high purity and can be used as a standard substance.

The method for preparing the pregabalin lactam methylene dimer provided by the present application has following advantages:

1. The yield of the pregabalin lactam methylene dimer can reach between 35% and 50% by using the method for preparing the pregabalin lactam methylene dimer provided by the present application, which is a great improvement. Compared with the traditional methods, the yield can be improved by more than one hundred times.

2. In the preparation method provided by the present application, after the reaction is completed, the content of the target product in the reaction system, the pregabalin lactam methylene dimer, can reach between 43% and 58%, and the remaining components are mainly unreacted pregabalin, as well as the by-products, pregabalin lactam and N-methyl pregabalin lactam, the retention behaviors of which differ greatly, and thus the separation difficulties are greatly reduced.

3. In the preparation method provided by the present application, the reaction solvent used can be a polar organic solvent such as methanol, ethanol, acetonitrile, N,N-dimethylformamide, or a mixed solvent of the polar organic solvent and water, which does not relate to the rarely used solvents or expensive organic solvents. The chiral center of the product is stable under acidic conditions and will not undergo isomerization.

4. In the whole preparation process, no special equipment and special raw materials are required. The preparation period is short, and the operation is simple with low cost.

DESCRIPTION OF THE DRAWINGS

In order to illustrate the examples of the present application and the technical solutions of the prior art more clearly, the drawings used in the examples and the prior art are briefly described below. Obviously, the drawings in the following description are only some examples of the present application. For those ordinary skilled in the art, other drawings can be also obtained according to these drawings without any creative work.

DETAILED DESCRIPTION OF THE INVENTION

Figure 1:
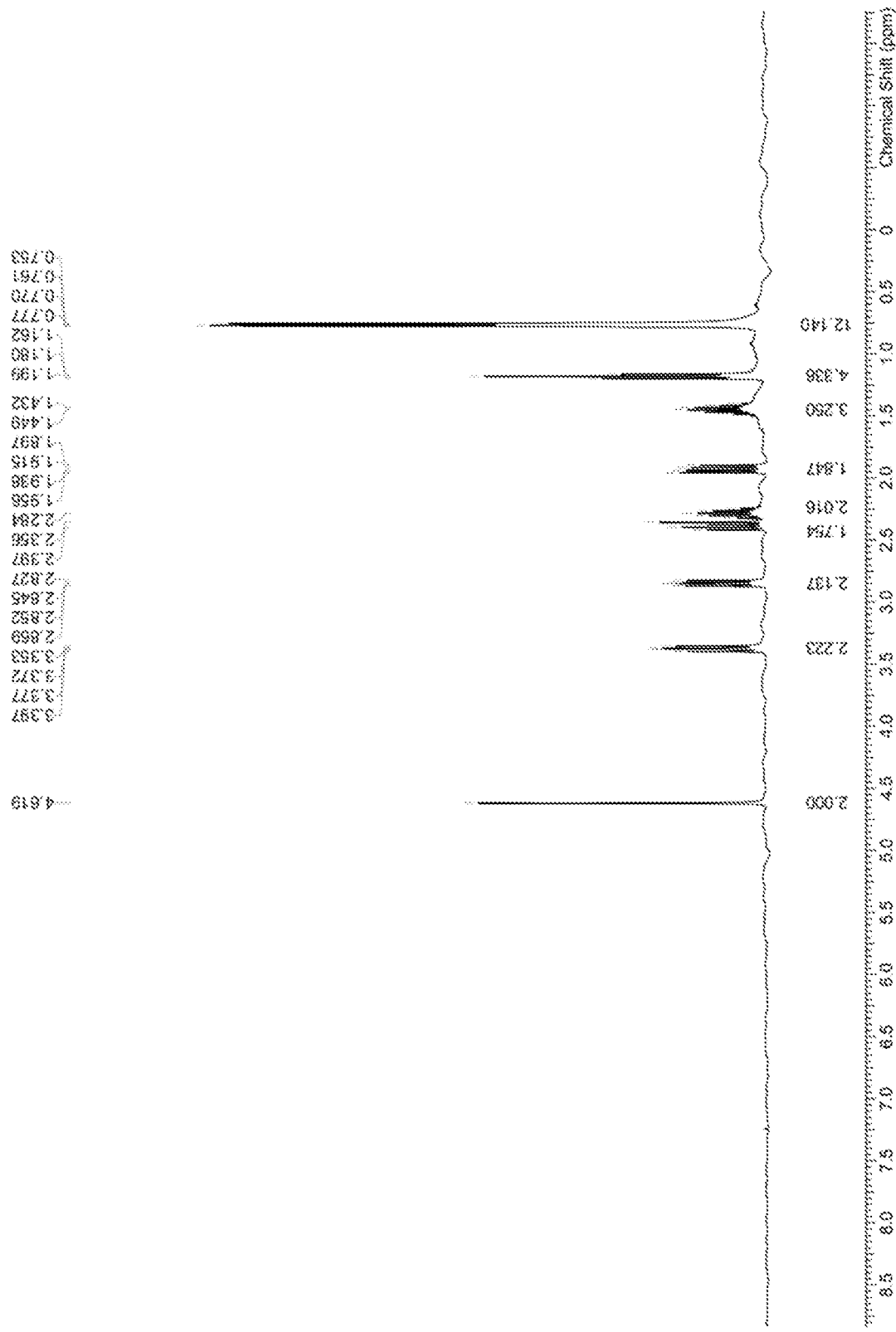
FIG. 1 The hydrogen nuclear magnetic resonance spectrum ($^1$H-NMR) of the pregabalin lactam methylene dimer prepared in the present application.
Figure 2:
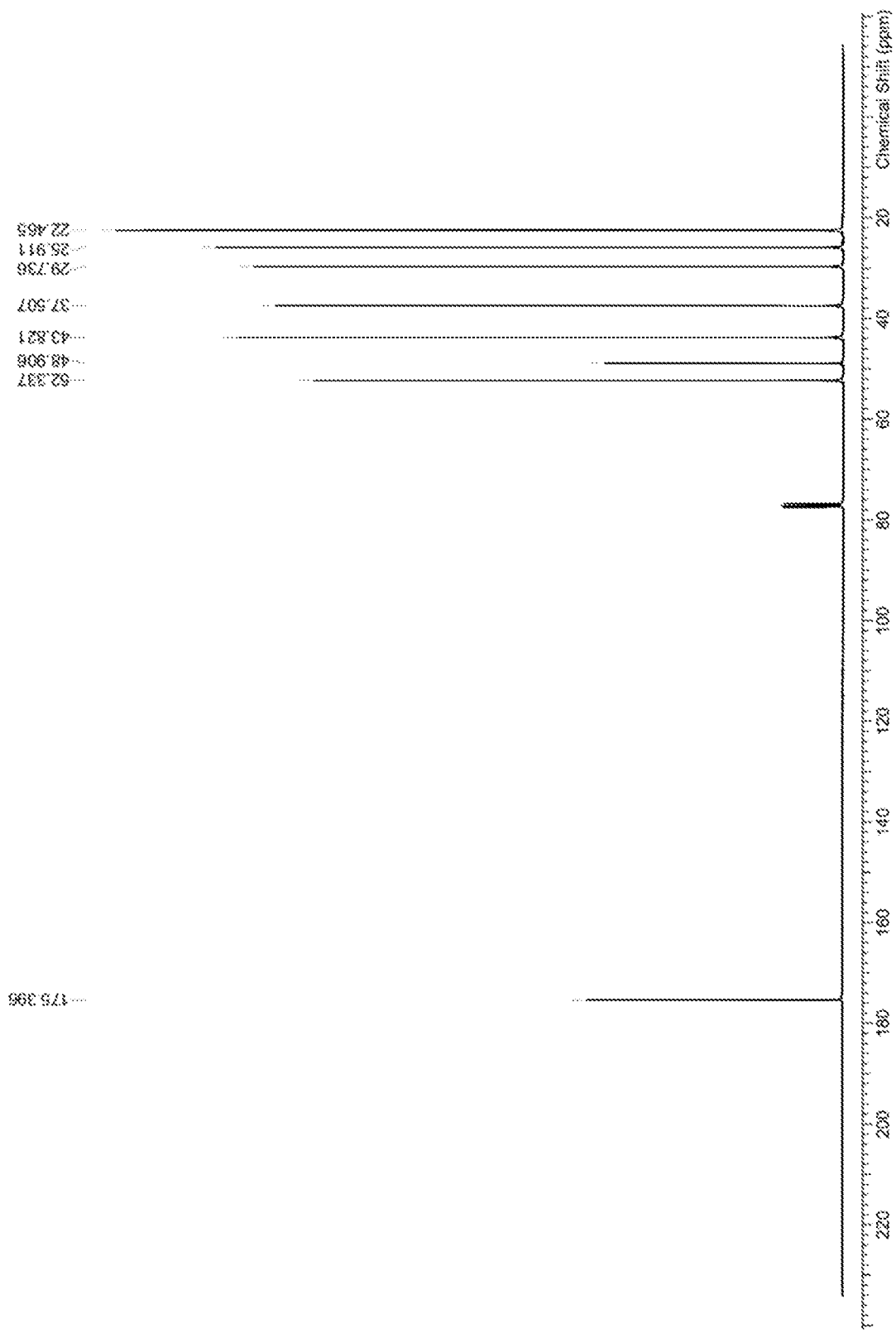
FIG. 2 The carbon nuclear magnetic resonance spectrum ($^{13}$C-NMR) of the pregabalin lactam methylene dimer prepared in the present application.
Figure 3:
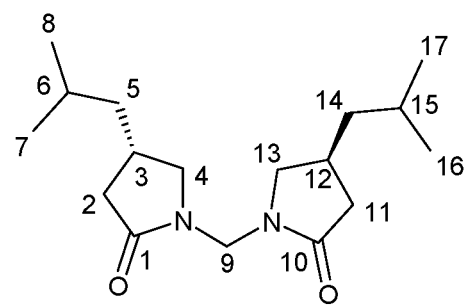
FIG. 3 The numbers of atoms in the structural formula of the pregabalin lactam methylene dimer prepared in the present application.
Figure 4:
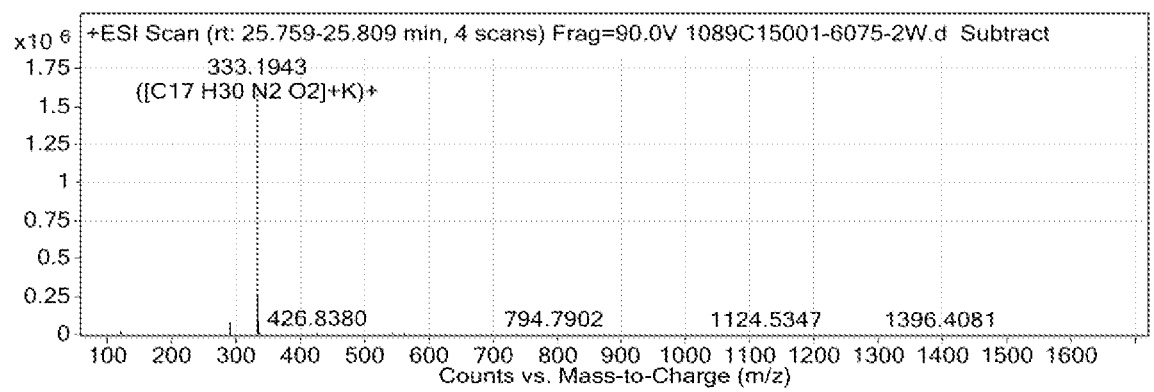
FIG. 4 The spectrum of combined high performance liquid chromatograph-high resolution mass spectrometry of the pregabalin lactam methylene dimer prepared in the present application.

In order to illustrate the purpose, technical solutions, and advantages of the present application more clearly, the present application will be further described in detail with reference to the accompanying drawings and examples. Obviously, the described examples are only a part of the examples of the present application, rather than all of the examples. Based on the examples of the present application, all other examples obtained by those ordinary skilled in the art without any creative effort shall fall within the protection scope of the present application.

Example 1

10.0 g of pregabalin (0.0628 mol) was added to 100 ml of methanol. 4.0 ml of formic acid (0.0912 mol) was added and stirred to dissolve, and then 6.0 ml of 30% (mass fraction) formaldehyde solution (0.0659 mol) was added, which was heated to a temperature of 60° C. to react for 18 hours, with the reaction system monitored by HPLC. When the content of the pregabalin lactam methylene dimer was 52%, the solvent was distilled under reduced pressure to obtain a solid. The solid was separated by column chromatography [HP-Silica normal phase silica gel, the eluent was n-hexane:ethyl acetate=(12:1), V/V] to obtain 7.95 g of the pregabalin lactam methylene dimer, with HPLC purity of 99.2% and a yield of 43%.

Example 2

10.0 g of pregabalin (0.0628 mol) was added to 120 ml of ethanol. 5.6 ml of glacial acetic acid (0.0979 mol) was added and stirred to dissolve, and then 5.0 ml of 30% formaldehyde solution (0.0549 mol) was added, which was heated to a temperature of 60° C. to react for 18 hours, with the reaction system monitored by HPLC. When the content of the pregabalin lactam methylene dimer was 44%, the solvent was distilled under reduced pressure to obtain a solid. The solid was separated by preparative liquid chromatography [column: YMC-Pack ODS-AQ, 250×20 mm, 5 μm, mobile phase A was water, mobile phase B was acetonitrile, mobile phase gradient: 0 min (40% B), 20 min (40% B), 30 min (60% B), 30.1 min (40% B), and 35 min (40% B), running time: 35 min] to obtain 7.02 g of the pregabalin lactam methylene dimer, with HPLC purity of 99.6% and a yield of 38%.

Example 3

10.0 g of pregabalin (0.0628 mol) was added to 150 ml mixture of water and methanol (the volume ratio of water:methanol was 1:1). 3.0 ml of trifluoroacetic acid (0.0404 mol) was added and stirred to dissolve, and then 2.1 g solid of metaformaldehyde (0.0233 mol) was added, which was heated to a temperature of 60° C. to react for 24 hours, with the reaction system monitored by HPLC. When the content of the pregabalin lactam methylene dimer was 56%, the pH of the reaction system was adjusted to about 8 with sodium carbonate solution, and the solvent was removed via lyophilization to obtain a solid. The solid was separated by column chromatography [HP-Silica normal phase silica gel, the eluent was n-hexane:ethyl acetate=(15:1, V/V)] to obtain 8.32 g of the pregabalin lactam methylene dimer, with HPLC purity of 99.2% and a yield of 45%.

Example 4

10.0 g of pregabalin (0.0628 mol) was added to 80 ml of dimethylsulfoxide. 4.2 ml of formic acid (0.0958 mol) was added and stirred to dissolve, and then 4.5 ml of 30% formaldehyde solution (0.0495 mol) was added, which was heated to a temperature of 60° C. to react for 14 hours, with the reaction system monitored by HPLC. When the content of the pregabalin lactam methylene dimer was 43%, the solvent was removed via lyophilization to obtain a solid. The solid was separated by preparative liquid chromatography [column: YMC-Pack ODS-AQ, 250×20 mm, 5 μm, mobile phase A was water, mobile phase B was acetonitrile, mobile phase gradient: 0 min (40% B), 20 min (40% B), 30 min (60% B), 30.1 min (40% B), and 35 min (40% B), running time: 35 min] to obtain 6.47 g of the pregabalin lactam methylene dimer, with HPLC purity of 99.1% and a yield of 35%.

Example 5

10.0 g of pregabalin (0.0628 mol) was added to 24 ml mixture of water and ethanol (the volume ratio of water:ethanol was 1:1). 3.0 ml of p-toluenesulfonic acid (0.0174 mol) was added and stirred to dissolve, and then 3.2 g of metaformaldehyde (0.0355 mol) was added, which was heated to a temperature of 70° C. to react for 16 hours, with the reaction system monitored by HPLC. When the content of the pregabalin lactam methylene dimer was 53%, the pH of the reaction system was adjusted to about 8 with sodium carbonate solution, and the solvent was removed via lyophilization to obtain a solid. The solid was separated by column chromatography [type: HP-Silica normal phase silica gel, the eluent was n-hexane:ethyl acetate=12:1, V/V] to obtain 8.68 g of the pregabalin lactam methylene dimer, with HPLC purity of 99.0% and a yield of 47%.

Example 6

10.0 g of pregabalin (0.0628 mol) was added to 120 ml methanol. 1.5 ml of methanesulfonic acid (0.0231 mol) was added and stirred to dissolve, and then 6.2 ml of 30% (mass fraction) formaldehyde solution (0.0681 mol) was added, which was heated to a temperature of 75° C. to react for 20 hours, with the reaction system monitored by HPLC. When the content of the pregabalin lactam methylene dimer was 58%, the pH of the reaction system was adjusted to about 8 with sodium carbonate solution, and the water was removed via lyophilization to obtain a solid. The solid was separated by column chromatography [type: HP-Silica normal phase silica gel, the eluent was n-hexane:ethyl acetate=10:1, V/V] to obtain 9.24 g of the pregabalin lactam methylene dimer, with HPLC purity of 99.2% and a yield of 50%.

Example 7

3.0 g of pregabalin (0.0188 mol) was added to 40 ml of N,N-dimethylformamide (DMF). 0.4 ml of 6N diluted hydrochloric acid (0.0024 mol) was added and stirred to dissolve, and then 1.2 ml of 30% formaldehyde solution (0.0132 mol) was added, which was heated to a temperature of 65° C. to react for 14 hours, with the reaction system monitored by HPLC. When the content of the pregabalin lactam methylene dimer was 46%, the pH of the reaction system was adjusted to about 8 with sodium carbonate solution, and the solvent was removed via lyophilization to obtain a solid. The solid was separated by preparative liquid chromatography [column: YMC-Pack ODS-AQ, 250×20 mm, 5 μm, mobile phase A was water, mobile phase B was acetonitrile, mobile phase gradient: 0 min (40% B), 20 min (40% B), 30 min (60% B), 30.1 min (40% B), and 35 min (40% B), running time: 35 min] to obtain 2.0 g of the pregabalin lactam methylene dimer, with HPLC purity of 99.4% and a yield of 36%.

Example 8

3.0 g of pregabalin (0.0188 mol) was added to 50 ml mixture of water and N-methylpyrrolidone (the volume ratio of water:N-methylpyrrolidone was 1:1). 0.4 ml of 6N diluted sulphuric acid (0.0024 mol) was added and stirred to dissolve, and then 0.7 g of metaformaldehyde (0.0078 mol) was added, which was heated to a temperature of 55° C. to react for 24 hours, with the reaction system monitored by HPLC. When the content of the pregabalin lactam methylene dimer was 47%, the pH of the reaction system was adjusted to about 8 with sodium carbonate solution, and the water was removed via lyophilization to obtain a solid. The solid was separated by column chromatography [type: HP-Silica normal phase silica gel, the eluent was n-hexane:ethyl acetate=15:1, V/V] to obtain 2.11 g of the pregabalin lactam methylene dimer, with HPLC purity of 99.0% and a yield of 38%.

The above examples are only preferred examples of the present application, which are not intended to limit the present application. Any modification, equivalent replacement and improvement made within the spirit and principle of the present application shall fall within the protection scope of the present application.

The invention claimed is:

1. A pregabalin lactam methylene dimer having the following structural formula:

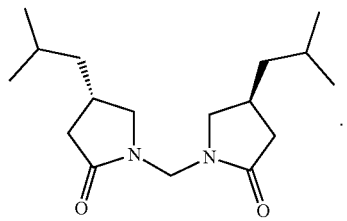 [SMILES: CC(C)C[C@H]1CC(=O)N(CN2C[C@@H](CC(C)C)CC2=O)C1]

2. A method for preparing a pregabalin lactam methylene dimer, comprising following steps:
(a) adding pregabalin, an acid and an aldehyde to a reaction solvent to obtain a reaction system;
(b) heating the reaction system to a temperature of 30-100° C. to react for 0.5-36 hours; and
(c) obtaining the pregabalin lactam methylene dimer after the reaction is completed; wherein, the pregabalin lactam methylene dimer has the following structural formula:

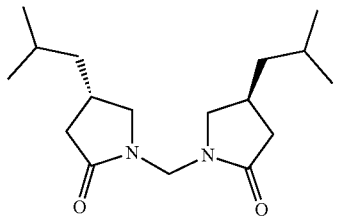

3. The method according to claim 2, wherein the reaction solvent in step (a) is selected from the group consisting of water, a polar organic solvent, and a mixture of water and the polar organic solvent.

4. The method according to claim 2, wherein the acid in step (a) is selected from the group consisting of an organic acid, an inorganic acid, and a combination thereof.

5. The method according to claim 2, wherein the aldehyde is selected from the group consisting of formaldehyde, formaldehyde dimer, metaformaldehyde and paraformaldehyde, or any combination thereof.

6. The method according to claim 2, wherein a molar ratio of the acid to pregabalin in step (a) is 0.01:1-50:1.

7. The method according to claim 2, wherein a molar ratio of the aldehyde to pregabalin in step (a) is 0.1:1-10:1.

8. The method according to claim 2, wherein the temperature of the reaction system in step (b) is 55-75° C., and the reaction is performed for 12-24 hours.

9. The method according to claim 1, wherein step (c) comprises: removing the reaction solvent to obtain a solid after the reaction is completed, and separating the solid to obtain the pregabalin lactam methylene dimer.

10. The method according to claim 9, wherein separating is performed by column chromatography or preparative liquid chromatography.

11. The method according to claim 3, wherein the polar organic solvent is selected from the group consisting of methanol, ethanol, propanol, isopropanol, acetonitrile, acetone, N,N-dimethylformamide, dimethylsulfoxide and N-methylpyrrolidone, or any combination thereof.

12. The method according to claim 4, wherein the organic acid is selected from the group consisting of formic acid, acetic acid, trifluoroacetic acid, methanesulfonic acid, ethanesulfonic acid, benzenesulfonic acid and p-toluenesulfonic acid, or any combination thereof and the inorganic acid is selected from the group consisting of hydrochloric acid, sulfuric acid, and phosphoric acid, or any combination thereof.

13. The method according to claim 5, wherein the aldehyde is formaldehyde or metaformaldehyde.

14. The method according to claim 6, wherein the molar ratio of the acid to pregabalin in step (a) is 0.1:1-2.5:1.

15. The method according to claim 7, wherein the molar ratio of the aldehyde to pregabalin in step (a) is 0.3:1-3:1.

* * * * *

UNITED STATES PATENT AND TRADEMARK OFFICE
CERTIFICATE OF CORRECTION

PATENT NO. : 12,018,018 B2
APPLICATION NO. : 17/291237
DATED : June 25, 2024
INVENTOR(S) : Jinsheng Lin et al.

It is certified that error appears in the above-identified patent and that said Letters Patent is hereby corrected as shown below:

In the Claims

Column 8, Claim 9, Line 35:
"according to claim 1,"
Should read:
--according to claim 2,--.

Column 8, Claim 12, Line 51:
"combination thereof and"
Should read:
--combination thereof; and--.

Signed and Sealed this
Tenth Day of September, 2024

Katherine Kelly Vidal
*Director of the United States Patent and Trademark Office*